United States Patent [19]

de Guelis et al.

[11] Patent Number: 4,696,496
[45] Date of Patent: Sep. 29, 1987

[54] SYSTEM FOR PUTTING TWO CONTIGUOUS ENCLOSURES INTO INDIVIDUAL COMMUNICATION WITH THE OUTSIDE

[75] Inventors: Hubert V. de Guelis, Le Pecq; Pascal Doute, Verneuil-sur-Seine, both of France

[73] Assignee: Societe Nationale Industrielle Aerospatiale, Paris, France

[21] Appl. No.: 789,152

[22] Filed: Oct. 18, 1985

[30] Foreign Application Priority Data

Oct. 31, 1984 [FR] France ............................. 84 16704

[51] Int. Cl.4 ............................................. F16L 39/00
[52] U.S. Cl. ................................ 285/137.1; 285/133.1; 285/130
[58] Field of Search .................. 285/137.1, 133.1, 130, 285/131

[56] References Cited

U.S. PATENT DOCUMENTS 2,956,586 10/1960 Zeigler et al. ............... 285/133.1 X
3,980,112 9/1976 Basham ........................ 285/133.1 X

FOREIGN PATENT DOCUMENTS 571701 3/1959 Canada ............................ 285/133.1
269735 4/1927 United Kingdom ............. 285/133.1
1253959 11/1971 United Kingdom .

Primary Examiner—Richard J. Scanlan, Jr.
Attorney, Agent, or Firm—Fisher, Christen & Sabol

[57] ABSTRACT

A system for putting two contiguous enclosures (2,3) disposed on one side of a common wall (4) into individual communication with the outside. According to the invention, a coaxial coupling part (1) is provided enabling two connections to be made. The coupling is suitable for use in heart prostheses.

8 Claims, 5 Drawing Figures

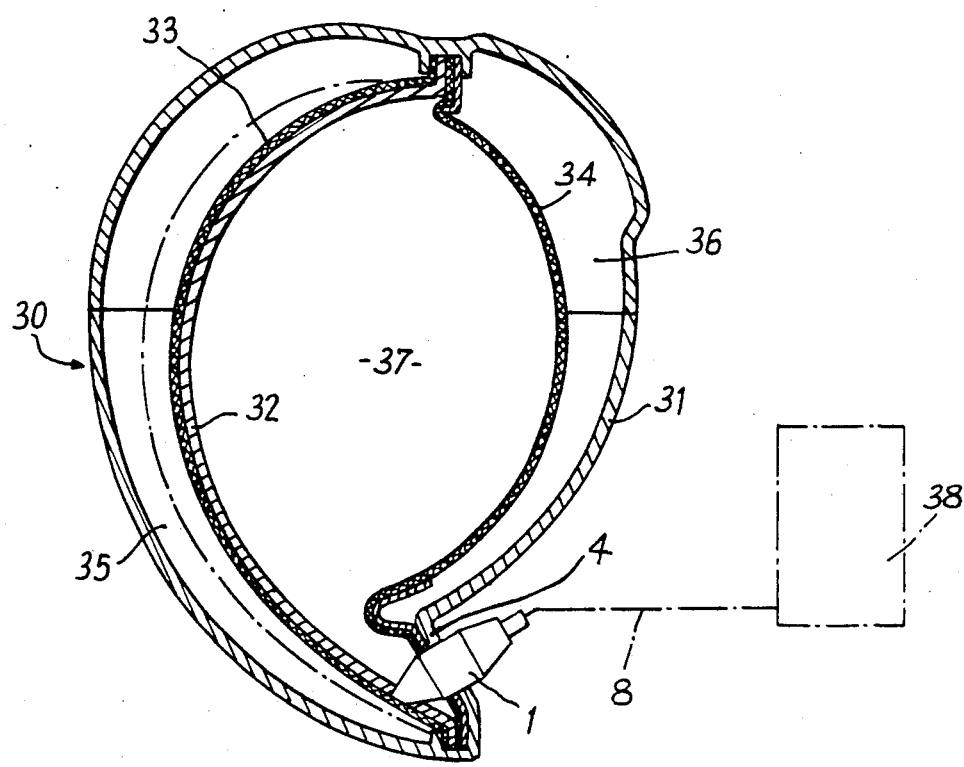

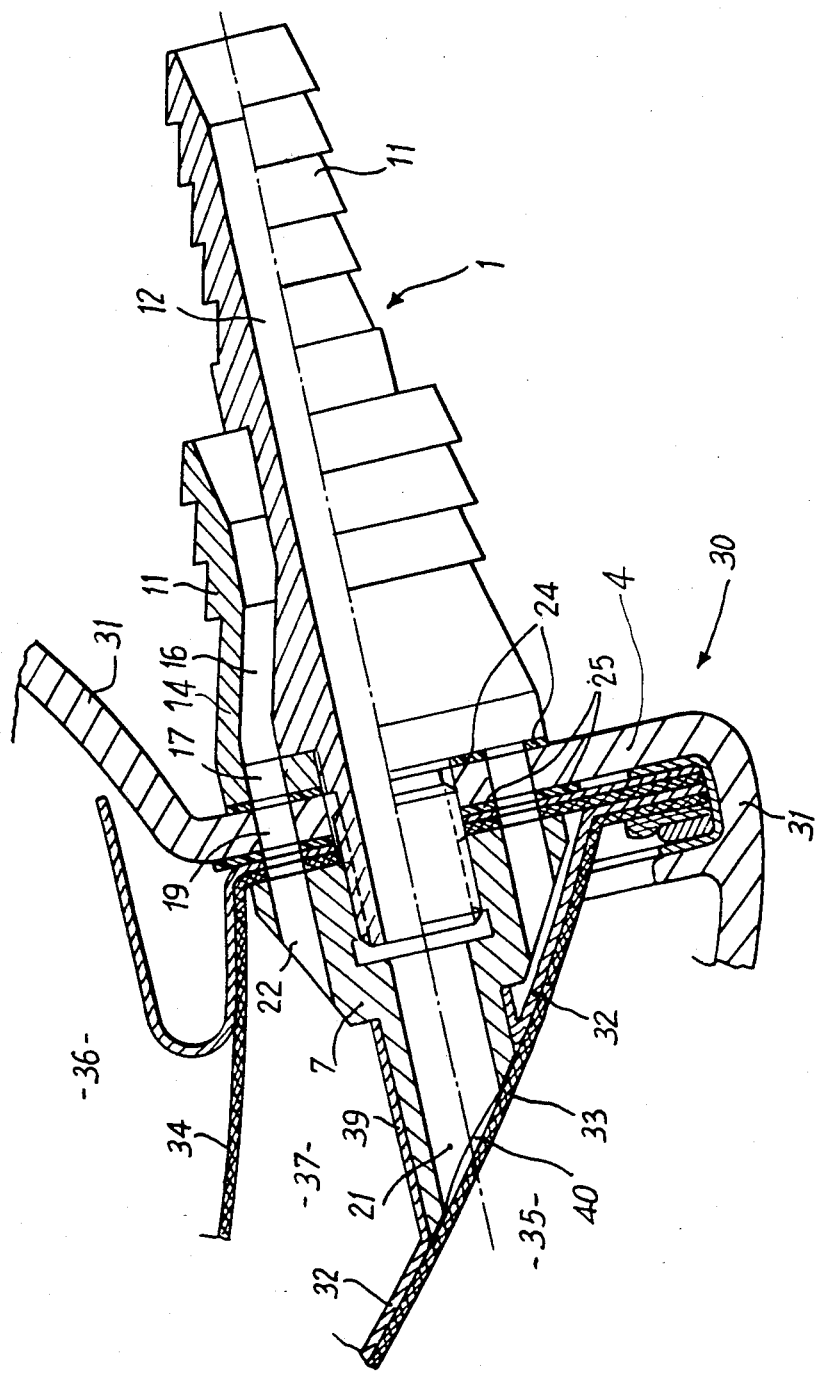

SYSTEM FOR PUTTING TWO CONTIGUOUS ENCLOSURES INTO INDIVIDUAL COMMUNICATION WITH THE OUTSIDE

The present invention relates to a system for putting two contiguous enclosures into individual communication with the outside, and also to a heart prosthesis provided with such a system.

BACKGROUND OF THE INVENTION

A heart prosthesis is already known, as described in European Pat. No. 0014130 for example, which comprises:

a pericardiac module comprising a housing which is divided into two chambers by a rigid partition, each of said chambers enclosing a pumping membrane which, together with the housing, delimits a blood pumping space representative of a ventricle of a natural heart to be replaced, and together with a partition delimits a control enclosure for a fluid for actuating the corresponding membrane; and a control device comprising at least one generator of fluid for supplying said control enclosures and connected thereto via a connection including a first pipe and a second pipe.

Thus, in such a heart prosthesis, it is necessary to connect each of the control enclosures to the fluid generator in order to actuate each of said membranes, i.e. in order to simulate the operation of the left ventricle and of the right ventricle of a natural heart.

In such a prosthesis, it is clear that the fluid generator must be disposed outside the human body so the connection with the prosthesis has to pass through the skin.

In order to simplify the passage through the skin and the inherent problems of compatibility, sealing to the skin, risk of infection, etc. . . . , it is particularly advantageous for such a connection to be constituted by only one apparent tube.

Further, this connection must be capable of allowing each of the membranes in the prosthesis to be controlled independently.

The object of the present invention is to solve these difficulties and to provide a coupling system for such a connection.

Although the invention has been presented above in the context of the particular application of a heart prosthesis, the system of the invention may naturally be used whenever it is desired to put two contiguous enclosures disposed on the same side of a common wall into individual communication with the outside.

SUMMARY OF THE INVENTION

The present invention provides a system for putting two contiguous enclosures disposed on the same side of a common wall into individual communication with the outside, said system comprising:

both a two-piece coupling part constituted by:
a first tubular end piece suitable for being coupled to a first pipe and provided with a first axially disposed passage in correspondence with a first opening provided in said common wall, said first end piece being intended to be mounted thereon, on the opposite side to said enclosures; and
a second end piece suitable for being coupled to a second pipe surrounding and enclosing said first pipe in such a manner as to provide an intermediate space between the outside wall of the first pipe and the inside wall of the second pipe, said second end piece being fixed to said first end piece, being coaxial therewith, and being disposed in such a manner as to include at least one second passage which is excentric relative to said first passage, and suitable for being put into communication with said intermediate space between the pipes and with a second opening provided through said common wall, said second end piece being intended to be mounted on said common wall on the side opposite to said enclosures;
and also a fixing part disposed on the same side as said enclosures and provided for fixing said coupling part to the said common wall, said fixing part including an axial passage opening out into one of said enclosures and intended to be put into communication with said first passage through said first end piece and said first opening through said common wall, together with at least one eccentric passage opening out into the other enclosure and intended to be put into communication with said second passage thorough said second end piece and said second opening through the common wall of the enclosures.

A coaxial coupling system is thus obtained allowing a coaxial fluid connection to be used. It may be observed, that when a coupling system in accordance with the invention is applied to connections to a heart prosthesis, it provides the advantage of rapid coupling to the generator of actuating fluid for said prosthesis, in addition to the above-mentioned advantages.

Advantageously, said first tubular end piece includes an extension passing through said first opening through the common wall and co-operating with said fixing part in order to mount said coupling part on said common wall of the enclosures. Said extension and the fixing part may be screwed together. In order to ensure that the various passages and openings are disposed opposite one another, any suitable marking or guidance system may be provided, for example a centering peg or flat.

In order to fix the pipes to the end pieces, the outside surfaces of the end pieces may include a set of corrugations of known type. Thus, when the pipes are fitted over the end pieces they cannot spontaneously become disengaged therefrom.

In order to facilitate connecting said pipes on the end pieces, it is advantageous for the first end piece to project beyond the second end piece away from said opposite side of the said common wall.

Said second passage through the second end piece may open out into the portion of the free face thereof which surrounds the first end piece. It is then advantageous for the first end piece to include a stop to prevent the end of the first pipe ahead of the free face of said second end piece. This prevents the second passage through the second end piece from being blocked by the end of said first pipe.

It is advantageous for the second end piece to be tubular and for its inside surface to delimit, together with the outside surface of the first end piece, an annular duct for being put into communication with the intermediate space between said first and second pipes, said first and second end pieces being fixed to one another by means of a transverse face which closes said annular duct, but through which said second passage passes.

It is often advantageous for said transverse face to include a plurality of second passages regularly distributed around the common axis of said end pieces, each of said second passages being associated with an opening in said wall common to the enclosures and with an excentric passage through the said fixing part.

Preferably, said transverse face presses against the common wall of the enclosures when said end pieces are mounted on the enclosures by means of the fixing piece.

The present invention also provides a heart prosthesis comprising:

a pericardiac module including a housing divided into two chambers by a rigid partition, each of said chambers enclosing a pumping membrane which, together with the housing, delimits a blood pumping space representative of a ventricle in a natural heart to be replaced, and together with said partition delimits a control enclosure for an actuating fluid for actuating the corresponding membrane; and a control device comprising at least one generator of fluid for feeding said control enclosures and connected thereto by a connection comprising a first pipe and a second pipe, the prosthesis including the improvement whereby:

said first and second pipes are disposed in such a manner that the second pipe surrounds and encloses the first in such a manner as to leave an intermediate space between its inside wall and the outside wall of said first pipe; and in that a coupling system is provided comprising:

both a two-piece coupling constituted by:
a first tubular end piece suitable for being coupled to said first pipe and provided with a first passage disposed axially and in communication with a first opening provided through the wall of said housing, said first end piece being intended to be mounted thereon, on the outside of said housing; and
a second end piece suitable for being coupled to said second pipe and fixed to said first end piece, said second end piece being coaxial with the first end piece and being disposed in such a manner as to include at least one second passage which is excentric relative to said first passage and suitable for being put into communication with said intermediate space between the pipes and with a second opening provided through said wall of the housing, said second end piece being intended to be mounted on said wall of the housing on the outside of said housing;

and also a fixing part disposed on the inside of the housing and provided for fixing said coupling part to said wall of the housing, said fixing part including an axial passage opening out into one of said control enclosures through said rigid partition and intended to be put into communication with said first passage through said first end piece and with said first opening through the wall of the housing, together with at least one excentric passage opening out in the other control chamber and intended to be put into communication with said second passage through said second end piece and with said second opening through said wall of the housing.

BRIEF DESCRIPTION OF THE DRAWINGS

Embodiments of the invention are described by way of example with reference to the accompanying drawings, in which identical references designate similar items, and in which:

FIG. 4 is a diagram of a heart prosthesis fitted with a coupling system in accordance with the invention; and FIG. 5 is a view on a larger scale and partially in section through the coupling system in accordance with the invention as mounted on the heart prosthesis of FIG. 4.

MORE DETAILED DESCRIPTION

Figure 1:
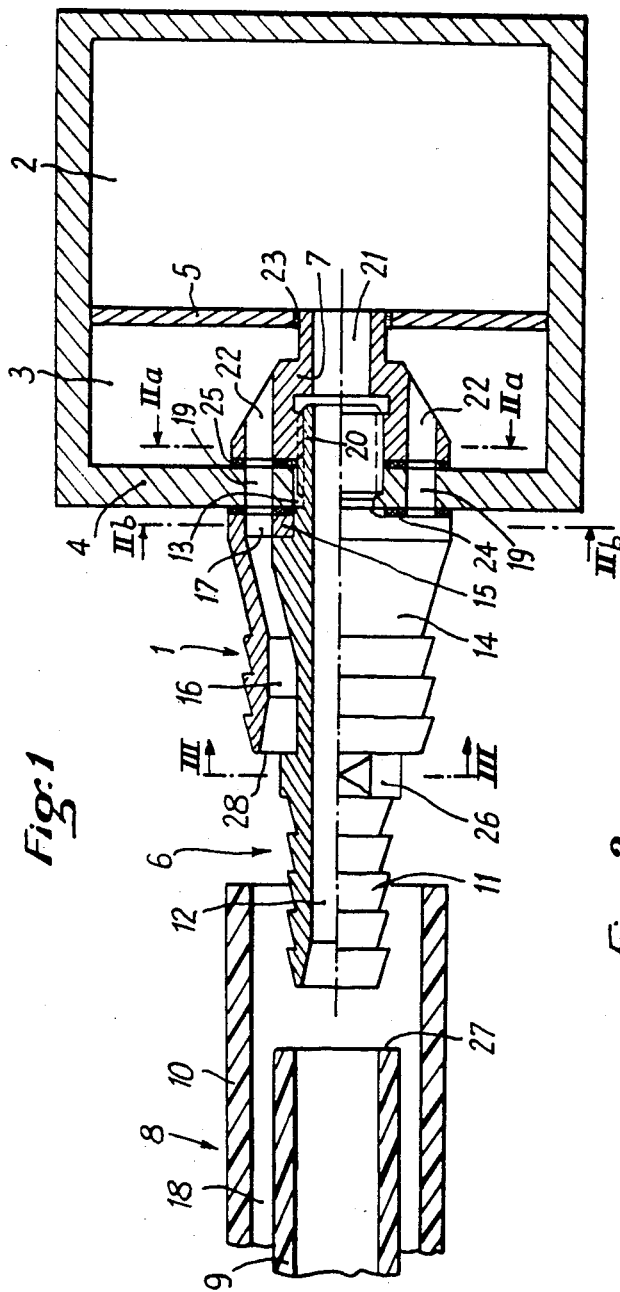
FIG. 1 is a diagrammatic view, in partial section, showing a coupling system in accordance with the invention.
Figure 3:
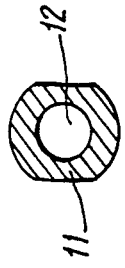
FIG. 3 is a section on line III—III of FIG. 1.
Figure 2:
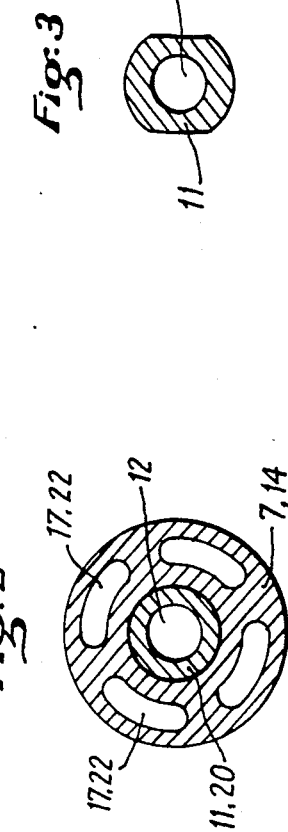
FIG. 2 is a section on either of lines IIa—IIa or IIb—IIb of FIG. 1.

The system 1 in accordance with the invention as shown in FIGS. 1 to 3 is intended to put two contiguous enclosures 2 and 3 disposed on one side of a common wall 4 individually into communication with the outside. The two enclosures 2 and 3 are separated from each other by a partition 5.

This system in accordance with the invention comprises a two-piece coupling part 6 and a fixing part 7.

The coupling part 6 is intended to be disposed on the other side of the common wall 4 to the enclosures 2 and 3, and to be coupled to a tubular connection 8 comprising an inside pipe 9 and an outside pipe 10.

The coupling part 6 comprises a first tubular end piece 11 suitable for being connected to the inside pipe 9 and provided with an axial passage 12 which is in communication with an opening 13 provided through the common wall 4. The coupling part 6 also comprises a second end piece 14 suitable for being connected to the outside pipe 10. The second end piece 14 is fixed to the first end piece 11 by means of an end face 15 applied against the outside face of the common wall 4. The end piece 14 includes an annular passage 16 and the face 15 has openings 17 in communication with said passage 16. Thus, the second end piece 14 is suitable for being connected to the intermediate space 18 provided between the pipes 9 and 10.

Further, the common wall 4 includes openings 19 having the same shape as the openings 17 and disposed in alignment therewith.

The two-piece coupling part 6 may be fixed to the wall 4 by means of the fixing part 7. To this end, the coupling part 6 includes a threaded tubular extension 20 passing through the hole 13 and on which the fixing part 7 may be screwed.

The fixing part includes an axial passage 21 opening out into the enclosure 2 and disposed in alignment with the passage 12, together with peripheral passages 22 opening out into the enclosure 3 and in alignment with the openings 17 and 19.

The fixing part is connected in sealed manner to the rim of a hole 23 provided through the partition 5.

Gaskets 24 and 25 including openings identical to the openings 17, 19, and 22, are provided firstly between the face 15 and the wall 4, and secondly between the wall 4 and fixing part 7.

It can thus be seen that a single coupling system 1 together with a single coaxial connection 8 may be used to connect both enclosures 2 and 3 to the outside.

The outside surfaces of the end pieces 11 and 14 are provided with corrugations, in known manner, in order to prevent the pipes 9 and 10 from being accidentally pulled away once they have been fitted over respective ones of the end pieces. The inner end piece 11 projects beyond the outer end piece 14, and the outer surface of the end piece 11 includes a stop 26 for engaging the leading end 27 of the inside tube 9. The leading end 27 is thus prevented from blocking the adjacent opening 28 to the annular passage 16.

FIG. 4 shows an application of the coupling system shown in FIGS. 1 to 3 to a heart prosthesis, for example to a prosthesis of the type described in European Pat. No. 0014130.

Such a heart prosthesis comprises a pericardiac module 30 comprising a housing 31 divided into two chambers by a rigid partition 32. A pumping membrane 33 or 34 is enclosed in each of said chambers and, together with the housing delimits a blood-pumping space 35 or 36 representative of a ventricle of a natural heart to be replaced. For example, the pumping space 35 correpsonds to the right ventricle whereas the space 36 corresponds to the left ventricle. Further, each of said membranes delimits, together with the rigid partition 32, a control enclosure for a gas for actuating the corresponding membrane. In FIG. 4, the membrane 33 is shown pressed against the partition 32, so one of the control enclosures is not visible in this figure. In contrast, the control enclosure provided between the partition 32 and the membrane 34 is referenced 37.

Further, the heart prosthesis includes a control device 38 including at least one generator of gas for feeding said control enclosures and connected thereto by a connection which, in accordance with the invention, is of the same type as the connection 8 shown in FIG. 1.

In FIG. 5, it can be seen that the coupling system 1 is mounted on the portion 4 of the wall 31 of the housing 30 in such a manner that the passages and orifices 16, 17, 19, and 22 provide communication between the enclosure 37 and the space 18 provided in the connection 8 between the pipes 9 and 10, and that the axial passages 12 and 21 put the inside of the pipe 9 into communication with the back of the membrane 33.

To this end, the partition 32 (which corresponds to the partition 5 in FIG. 1) is provided with a tube 39 extending a hole 40 provided through the partition 32 towards the system 1. Thus, when gas under pressure is sent from the generator 38 along the pipe 9 and the passages 12 and 21, said gas is capable of acting on the membrane 33 via the hole 40 through the partition 32. The connection between the tube 39 and the fixing part 7 is sealed.

As can be seen in FIGS. 4 and 5, a system is provided for clamping the periphery of the partition 32 together with the membranes 33 and 34.

It can be seen in FIGS. 4 and 5, a system is provided for clamping the periphery of the partition 32 together with the membranes 33 and 34.

It can thus be seen that a coaxial coupling system in accordance with the invention can be used to provide independent actuation of the membranes 33 and 34, via the pipe 9 and passages 12 and 21, or via the annular passage 18 and the passages 16, 17, 19, and 22. Further, such a coaxial system has an additional advantage over those mentioned above of being more compact than a device for two physically separate circuits. In order to ensure that the system is bio-compatible, the component parts thereof may be made of titanium.

It may be observed that the system in accordance with the invention does not cause head loss in the actuating fluid.

We claim:

1. A system for putting two contiguous enclosures disposed on the same side of a common wall into individual communication with the outside, wherein the system comprises:
 both a two-piece coupling part constituted by:
  a first tubular end piece suitable for being coupled to a first pipe and provided with a first axially disposed passage in communication with a first opening provided in said common wall, said first end piece having first connecting means and being intended to be mounted on said common wall, on the opposite side to said enclosures; and
  a second end piece suitable for being coupled to a second pipe surrounding and enclosing said first pipe in such a manner as to provide an intermediate space between the outside wall of the first pipe and the inside wall of the second pipe, said second end piece being fixed to said first end piece, being coaxial therewith, and being disposed in such a manner as to include at least one second passage which is eccentric relative to said first passage, and suitable for being put into communication with said intermediate space between the pipes and with a second opening provided through said common wall, said second end piece being intended to be mounted on said common wall on the side opposite to said enclosures;
 and also a fixing part disposed on the same side as said enclosures and provided with second connecting means for fixing said coupling part by way of said first connecting means to the said common wall, said fixing part including an axial passage opening out into one of said enclosures and intended to be put into communication with said first passage through said first end piece and said first opening through said common wall, together with at least one eccentric passage opening out into the other enclosure and intended to be put into communication with said second passage through said second end piece and said second opening through the common wall of the enclosures.

2. A system according to claim 1, wherein said first tubular end piece includes an extension adapted to pass through said first opening through the common wall and having said first connecting means cooperate with said fixing part second connecting means in order to mount said coupling part on said common wall of the enclosures.

3. A system according to claim 1, wherein said first end piece projects beyond said second end piece toward said pipes to be coupled.

4. A system according to claim 3, wherein said second passage communicates with an annular duct through said second end piece, said annular duct opening out into that portion of the free face of said second end piece which surrounds said first end piece.

5. A system according to claim 4, wherein said first end piece includes a stop for engaging the end of the first pipe ahead of the free face of said second end piece.

6. A system according to claim 1, wherein said second end piece is tubular, wherein its inside surface delimits, together with the outside surface of the first end piece, an annular duct for being put into communication with the intermediate space between said first and second pipes, and wherein said first and second end pieces are fixed to each other by means of a transverse face which partially closes said annular duct, but through which said second passage passes.

7. A system according to claim 6, wherein said transverse face includes a plurality of second passages regularly distributed around the common axis of said end pieces, each of said second passages being adapted to be associated with an opening in said wall common to the enclosures and with an excentric passage through the said fixing part.

8. A system according to claim 6 or 7, wherein said transverse face provides said two-piece coupling part with a bearing face adapted to be placed --. against the common wall of the enclosures.

* * * * *